(12) United States Patent
Noble et al.

(10) Patent No.: US 10,952,857 B2
(45) Date of Patent: Mar. 23, 2021

(54) IMPLANT WITH POROUS OUTER LAYER

(71) Applicant: Poriferous, LLC, Newnan, GA (US)

(72) Inventors: Aaron Noble, Newnan, GA (US); Jaing Qian, Shanghai (CN)

(73) Assignee: Poriferous, LLC, Newnan, GA (US)

( * ) Notice: Subject to any disclaimer, the term of this patent is extended or adjusted under 35 U.S.C. 154(b) by 0 days.

(21) Appl. No.: 14/819,758

(22) Filed: Aug. 6, 2015

(65) Prior Publication Data

US 2016/0038289 A1 Feb. 11, 2016

Related U.S. Application Data

(60) Provisional application No. 62/042,085, filed on Aug. 26, 2014, provisional application No. 62/034,014, filed on Aug. 6, 2014.

(51) Int. Cl.
*A61F 2/28* (2006.01)
*A61L 27/14* (2006.01)
*A61L 27/34* (2006.01)
*A61L 27/56* (2006.01)
*B29D 11/02* (2006.01)
*B29K 105/04* (2006.01)

(52) U.S. Cl.
CPC .......... *A61F 2/2875* (2013.01); *A61F 2/2846* (2013.01); *A61L 27/14* (2013.01); *A61L 27/34* (2013.01); *A61L 27/56* (2013.01); *B29D 11/023* (2013.01); *A61F 2002/2817* (2013.01); *A61F 2002/2878* (2013.01); *A61L 2430/02* (2013.01); *A61L 2430/16* (2013.01); *B29K 2023/06* (2013.01); *B29K 2105/04* (2013.01); *B29K 2995/0056* (2013.01)

(58) Field of Classification Search
CPC ............ A61F 2/2875; A61F 2002/2878; A61F 2002/30013; A61F 2250/0024; A61F 2002/30242; A61F 2230/0071; A61F 2002/30968; A61F 2/141
See application file for complete search history.

(56) References Cited

U.S. PATENT DOCUMENTS

| 5,089,021 A | 2/1992 | Vachet |
| 5,584,880 A | 12/1996 | Martinez |
| 7,407,510 B2 * | 8/2008 | Perry .................. A61F 2/141 623/23.75 |
| 8,206,450 B2 * | 6/2012 | Henry ................. A61L 27/48 623/17.17 |

(Continued)

OTHER PUBLICATIONS

International Search Report and Written Opinion, PCT Application No. PCT/US2015/043968, dated Oct. 15, 2015.

(Continued)

*Primary Examiner* — Bruce E Snow
*Assistant Examiner* — Melissa A Hoban
(74) *Attorney, Agent, or Firm* — Kilpatrick Townsend & Stockton LLP

(57) ABSTRACT

Embodiments of the invention described herein thus provide implants and methods for manufacturing an implant having an outer cortical layer that is porous. The porous outer cortical layer can help encourage tissue ingrowth into the implant. The porous outer cortical layer may be positioned around a core structure this is solid or that has a hollow interior. The core structure may be spherical or any other appropriate shape for a medical implant.

17 Claims, 11 Drawing Sheets

(56) References Cited

U.S. PATENT DOCUMENTS

| | | | |
|---|---|---|---|
| 2004/0243237 A1 | 12/2004 | Unwin et al. | |
| 2006/0224242 A1* | 10/2006 | Swords | A61B 17/8085 623/17.19 |
| 2009/0068245 A1* | 3/2009 | Noble | A61F 2/2875 424/423 |
| 2013/0199748 A1* | 8/2013 | Christensen | B22F 3/1055 164/494 |

OTHER PUBLICATIONS http://www.eyeplastics.com/ocular-implants-silicone-hydroxyapatite-medpor-bio-ceramic.html, 2012.
International Preliminary Report on Patentability, PCT Patent Application No. PCT/US2015/043968, dated Feb. 16, 2017, 9 pages.
Office Action, European Patent Application No. 15760319.2, dated May 17, 2018, 6 pages.

\* cited by examiner

IMPLANT WITH POROUS OUTER LAYER

CROSS REFERENCE TO RELATED APPLICATIONS

This application claims the benefit of U.S. Provisional Application Ser. No. 62/034,014, filed Aug. 6, 2014, titled "Hollow Implant" and U.S. Provisional Application Ser. No. 62/042,085, filed Aug. 26, 2014, titled "Implant," the entire contents of each of which are hereby incorporated by reference.

FIELD OF THE DISCLOSURE

Embodiments of the present disclosure relate generally to an implant having an outer cortical layer that is porous. The porous outer cortical layer can help encourage tissue ingrowth into the implant. The porous outer cortical layer may be positioned around a core structure this is solid or that has a hollow interior. The core structure may be spherical or any other shape.

BACKGROUND

Craniofacial surgery generally includes restructuring a damaged portion of a patient's bone or other tissues. For example, ocular implants such as spheres can be used in connection with enucleation and evisceration procedures. In one example, the orbit is the boney socket in the skull that contains and houses the eye, along with the associated structures that support eye function, such as the eye muscles, nerves, and blood vessels. In some instances, a variety of problems can occur in the eye socket, ranging from inflammatory diseases or other diseases, tumors, infections, birth defects, or injuries from trauma. When these problems occur, it may become necessary to reconstruct various portions of the orbital socket, including implantation of ocular implants, such as orbital spheres.

In some instances, it is desirable for an implant to allow fibrovascular ingrowth such that it becomes integrated with the patient's own tissues. It is generally accepted that providing ocular implants made of biocompatible porous material can help encourage vascularization and tissue ingrowth. Various materials for orbital implants have included silicone, high density polyethylene, porous alumina, and hydroxyapatite. However, improvements to surgical implants and materials are desirable.

BRIEF SUMMARY

Embodiments of the present disclosure relate generally to an implant having an outer cortical layer that is porous. The porous outer cortical layer can help encourage tissue ingrowth into the implant. The porous outer cortical layer may be positioned around a core structure this is solid or that has a hollow interior. The core structure may be spherical or any other shape, such as elongated, plate-shaped, curved, or any other appropriate shape. The porous outer cortical layer and a supporting core (if provided) may be generally formed of the same or a similar material, such that they may be thermally bonded to one another. In one specific example, the core and cortex are sintered to one another.

For example, there may be provided an implant, comprising: a core material comprising an outer surface that functions as a barrier to tissue ingrowth; a porous outer cortical layer sintered to and at least partially surrounding the core material, wherein the porous outer cortical layer allows tissue ingrowth. The core material may be formed as a hollow body or as a solid body. The core material and the porous outer cortical layer may be thermally processed via heat and compression. In use, fibrovascular ingrowth is allowed to occur into the porous outer cortical layer but is discouraged from extending past the barrier to tissue ingrowth.

Embodiments also provide a method of manufacturing an implant, comprising: forming a core material having a plurality of registering members extending therefrom; positioning the core material in a mold; applying a porous polymeric material around the core material in the mold, such that the porous polymeric material at least partially covers the core material; applying heat and pressure to sinter the porous polymeric material to the core material.

In another example, there is provided a method of manufacturing an implant, comprising: providing a plurality of individual articles having differing porosities, wherein the individual articles form a generally spherical implant; assembling the plurality of individual articles in a mold; applying heat and pressure to sinter the plurality of individual articles to one another.

In other embodiments, the implant is formed as a hollow body having an interior coating, such that outer surface of the hollow body allows tissue ingrowth and the interior coating prevents further ingrowth. In one example, the hollow body may be manufactured from two halves that are thermally processed together, the hollow body halves comprising an interior coating that prevents tissue ingrowth, and a porous outer surface that encourages tissue ingrowth.

DETAILED DESCRIPTION

Figure 1:
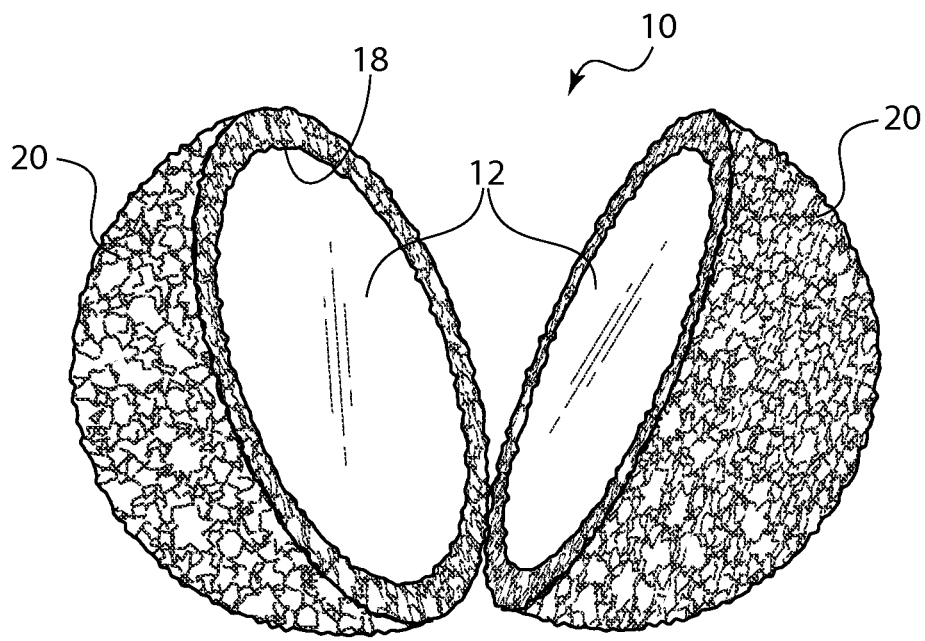
FIG. 1 shows a perspective view of an implant according to one embodiment described herein, cut in half to show a solid core material and an outer porous cortical layer.
Figure 2:
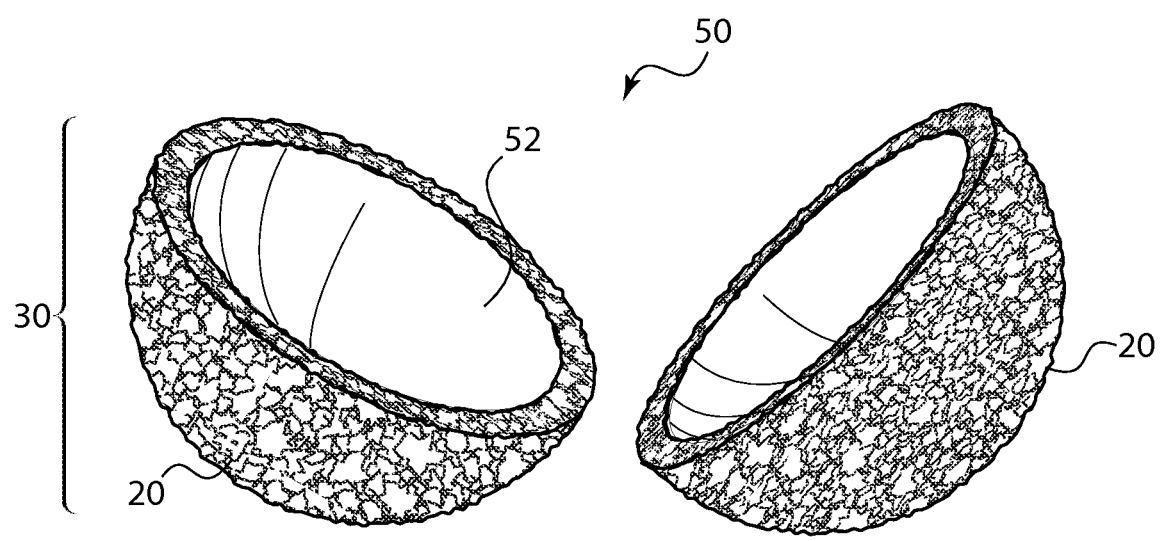
FIG. 2 shows a perspective view of an implant according to an alternate embodiment, having an inner coating on the porous cortical layer.

Specific embodiments of the present invention provide an implant having a porous outer cortical layer. The implant finds particular use in non-load bearing applications and reconstructions for the craniofacial skeleton and surrounding structures. As shown in FIG. 1, one embodiment of the implant 10 may have a core 12 surrounded or at least partially covered by a porous outer cortical layer 20. The core 12 may be solid or hollow. As shown in FIG. 2, another embodiment may provide a hollow implant 50 having an outer porous cortex or (outer cortical layer) 20 (for promoting tissue ingrowth) and an interior coating or layer 52 that is non-porous for preventing further tissue ingrowth past the interior coating 52.

Both embodiments allow fibrovascular ingrowth into the outer cortex 20 of the implant 10, 50, but prevent the ingrowth from extending into a core or interior of the implant 10, 50. While not wishing to be bound to any theory, it is believed that providing a porous external layer limits the depth of tissue integration into the implant without leaving a non-fully vascularized void in the center. It is believed that providing a generally thin cortical layer for ingrowth of tissue allows tissue ingrowth to occur more quickly. The ingrowth stops once it reaches the core 12 of implant 10, or the coating/layer 52 of implant 50. With quicker vascularization of the implant, a reduction of infection and related possible complications may be achieved.

Figure 3:
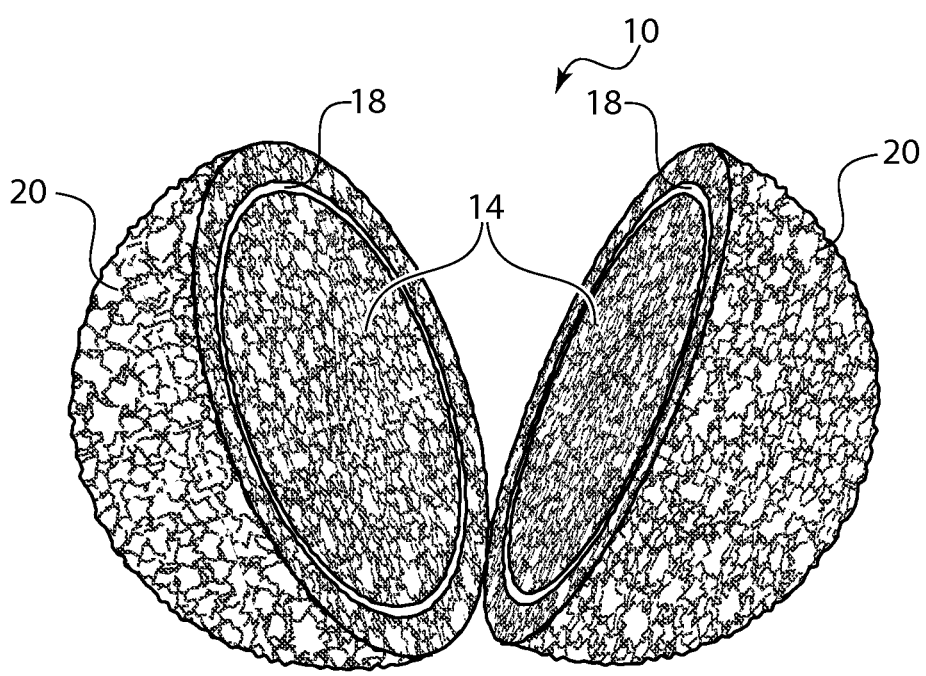
FIG. 3 shows a perspective view of an implant cut in half to show a porous core material and an outer porous cortical layer.
Figure 4:
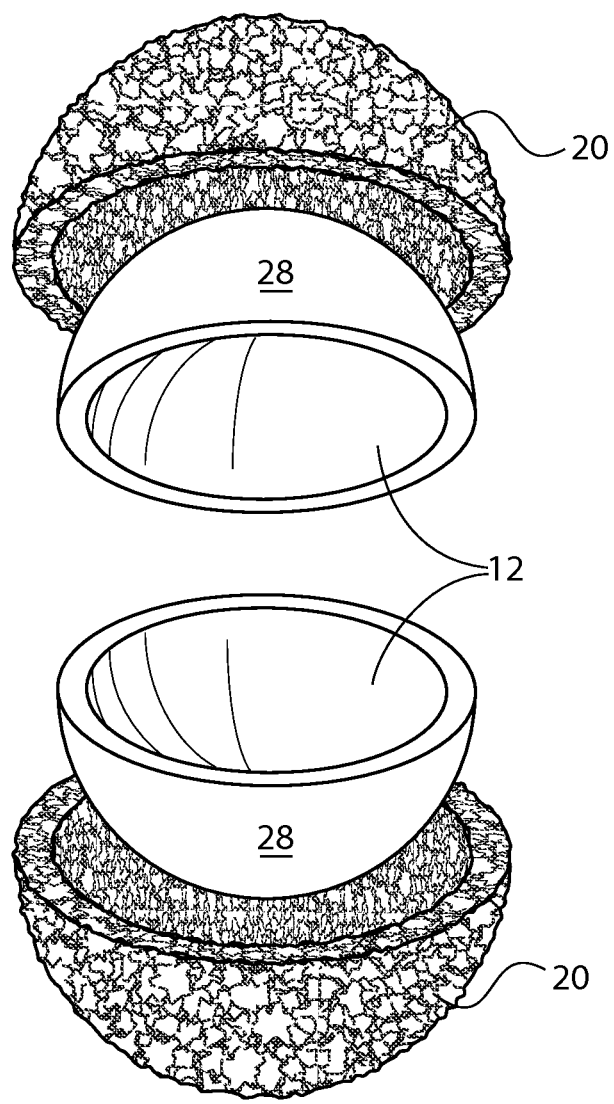
FIG. 4 shows an exploded view of an implant made from two hollow half spheres of a solid material, with a cortical material applied thereto.
Figure 5:
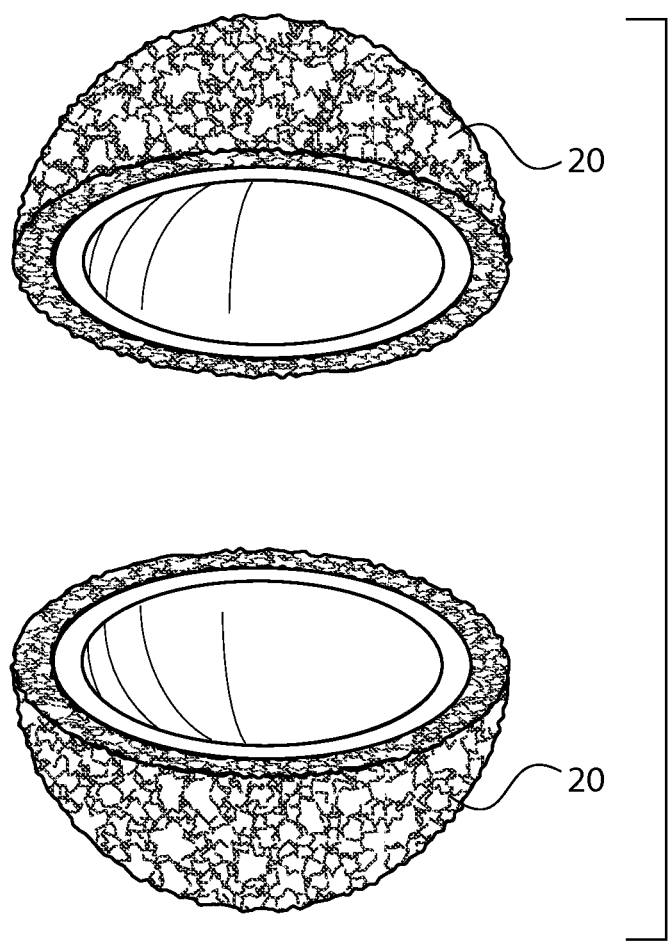
FIG. 5 shows the implant of FIG. 4 cut in half.

Referring first to the core 12/cortex 20 embodiment, the porous outer cortical layer 20 may be thermally bonded to the core 12. In one example, the core 12 may be a solid core, as shown by FIG. 1. In another example, the core 12 may be a porous polymer sphere implant formed as a non-hollow body 14 (i.e., a body that has porous material throughout), as shown by FIG. 3. The body 14 may be generally porous with a non-porous surface 18. In other examples, the core may be a hollow core. The hollow core may be a solid material, as shown by FIGS. 4 and 5. For example, the core 12 may be a silicone body. In another example, the hollow core may be a hollow porous polymer sphere implant formed as a hollow body 16, as shown by FIG. 5. In a further example, the core 12 may have any other appropriate shape or material. Although in the examples shown, the core 12 is illustrated as having a spherical shape, it should be understood that the core 12 may have any appropriate shape for the desired implant. For example, it may be an elongated rod if designed for use along a longer bone, a curved form, a plate form, or any other appropriate shape.

In some examples, the implants described herein may be used to stabilize, support, and provide space maintenance for bone graft materials in the maxilla, mandible zygoma, and other craniomaxillofacial areas. In other examples, implants may be used in the vertebral space, within the space between vertebral bodies. Other examples of uses of embodiments of implants described herein include but are not limited to surgeries involving long bones or portions of appendages such as the legs and arms, or a rib or any other bone or cavity.

For purposes of illustration, a spherical implant 10, 50 is described for the remainder of this disclosure. Various methods for manufacturing a spherical core 12 are outlined further below. The core may be designed so that it is not susceptible to leakage to fluid migrating into the core. The core may be designed so that it will maintain its shape, delaying the need for replacement of the implant.

In one example, the core 12 may be provided with an outer surface 18 that is smooth or otherwise non-porous. Such as outer surface 18 prevents, discourages, or limits vascular ingrowth or integration. The outer surface 18 forms what will eventually be an internal layer of solid (non-porous) material of the implant 10 that serves as a barrier to tissue/bone ingrowth.

Figure 7:
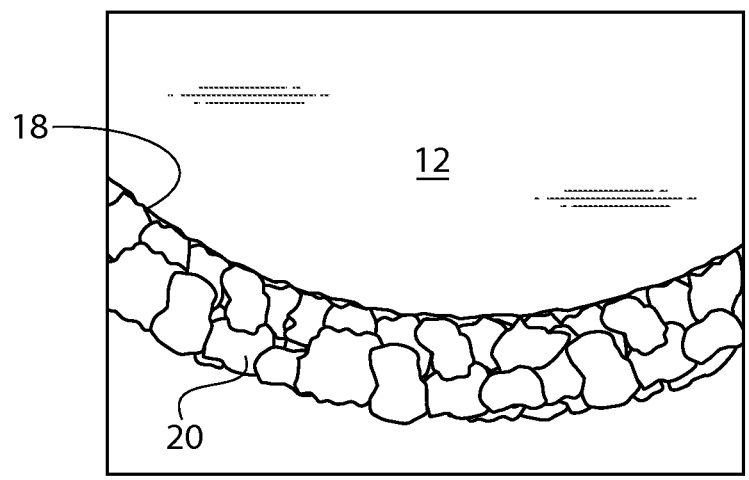
FIG. 7 shows a close-up view of a core having a porous outer cortical layer, illustrating one example of the layer thickness.

Surrounding the core 12 may be a porous outer cortical layer 20. The porous outer cortical layer 20 may have a porous structure that encourages fibrovascular ingrowth or integration into the porous outer cortical layer 20. The porous outer cortical layer 20 may fully encapsulate the core. Alternatively, the porous outer cortical layer 20 may only at least partially encapsulate the core. FIG. 7 illustrates a cross-sectional view of a portion of a core 12 with a non-porous outer surface 18 having a surrounding porous outer cortical layer 20. In one example, the porous outer cortical layer 20 may be thermally bonded to the outer surface 18 of the core 12.

Figure 8:
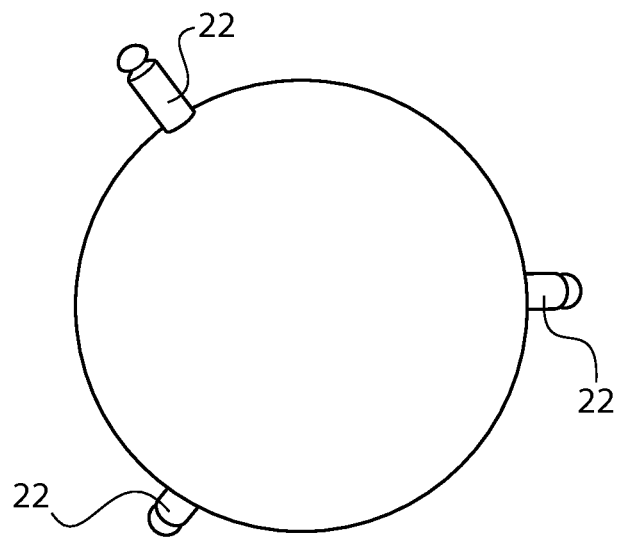
FIG. 8 shows a core with registering features, for use during one manufacturing method described herein.

In one embodiment, the core 12 may be provided with a plurality of registering features 22 that are designed to hold the core 12 in a center of a mold cavity. FIG. 8 illustrates a core 12 having three generally equally spaced registering features 22. It should be understood that more or fewer features 22 may be provided. The registering features 22 may be formed as extending pegs. They may be porous or non-porous. In use, the registering features 22 can help center the core 12 with respect to a mold cavity in order to allow space between the mold cavity and the outer surface 18 of the core 12. The interior shape of the mold cavity may be spherical in order to properly form the core 12. Beads, particles, or fines of the material that will form the porous outer cortical layer 20 may be delivered to the mold, such that they fill spaces around the core 12. The material also fills spaces around the registering features 22. Application of compression and heat via thermal processing may then cause sintering of the material to the core 12. This creates an over molded porous cortical layer 20. The heat and compression of the thermal process may cause the core 12 and the outer cortical layer 22 become sintered together, such that they are connected as a one-piece, integral implant.

As shown in FIG. 7, the layer 20 may be up to about two or three beads or particles thick. It is possible for the layer 20 to be thinner than three beads or particles thick. It is also possible for the layer 20 be thicker than three beads or particles thick. As an example only, it is possible for the porous outer cortical layer 20 to be between about 0.5 to about 1.5 mm thick. In a specific embodiment, the layer 20 may be about 0.8 to about 0.9 mm thick. (Of course, it is understood that the thickness of the layer 20 is dependent upon the diameter of the core. In these examples, the core is generally about 4-6 mm in diameter. Other core sizes may be provided, and it is understood that the thickness of the layer 20 may be adjusted accordingly.) In another embodiment, the core may be from about 1-10 mm in diameter, and the porous outer cortical layer 20 may be from about 2-5 mm thick.

In some embodiments, the implant may comprise a single sintered polymeric layer. In other embodiments, the implant may comprise a plurality of sintered polymeric layers. It is possible for each of the plurality of layers to be constructed independently of another layer. They may be provided by multiple thermal processes. As a result, it is possible to provide layers of an implant that demonstrate different polymers, pore sizes, or any other features.

The general goal is for the porous outer cortical layer 20 to have a thickness that allows tissue ingrowth. However, the thickness of the porous outer cortical layer 20 also limits the depth that the tissue integration may reach, due to its contact with the outer surface 18 of the core 12, which does not support tissue integration any further into the implant 10. In use, the porous outer cortical layer 20 limits the depth of tissue integration into the implant 10 without leaving a non-fully vascularized void in the center of the implant 10. By contrast, in a thick porous implant that is porous completely throughout, the center of the implant generally does not achieve 100% vascularization, which can leave an area of the implant full of fluid which can possibly produce lead to infections.

Figure 9:
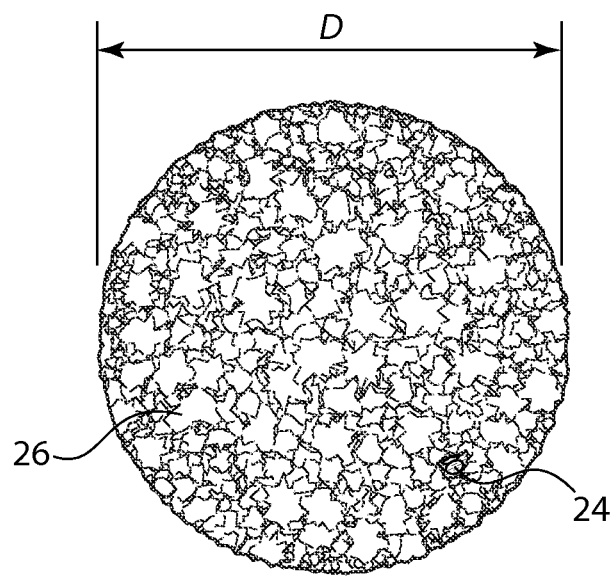
FIG. 9 shows one embodiment of an implant outer surface.

It can be desirable for the porous outer cortical layer 20 to extend up to and generally along the length of the registering features 22. In some examples, the registering features 22 may be about 0.5 to about 1.5 mm long. In other examples, the registering features 22 may be up to about 3 mm long. FIG. 9 illustrates a formed implant 10 having a diameter D that is equal to that of the diameter of the core 12 plus the thickness of the layer 20. This implant 10 is also shown having a slight registration mark 24 along the implant outer surface of 26. The registration mark 24 is the tip of one of the registering features 22. The registration mark 24 may have a diameter and/or shape that is generally equal to that of one to three particles in size, respective to the particle size of the material used. This results in a non-obvious registration mark 24 on the finished cortex article/implant 10.

Prior to applying the porous outer cortical layer 20 to the core 12, the core 12 may be manufactured using any appropriate manner. If the core 12 is provided as a hollow body 16, it may be compression molded, injection molded, blow molded, rotational molded, or formed using any other appropriate manufacturing technique. If the core 12 is provided as a solid, non-hollow body 14, it may be manufactured using any appropriate techniques, non-limiting examples of which are described further below.

The core 12 may be provided in any appropriate material. Non-limiting examples include porous polyethylene, polypropylene, medical grade silicone, or any combinations thereof. In one embodiment, implants comprise polyolefins, polymers, polyamides, polyesters, polyurethanes, polyimides, polyacrylonitriles, polycarbonate, poly methyl methacrylate (PMMA), polytetrafluoroethylene (PTFE), polyvinylidene fluoride (PVDF), polyketones, polysulfones, polyetherimides, or combinations or copolymers thereof. In some embodiments, a polyolefin may comprise polyethylene, polypropylene, or combinations or copolymers thereof. Polyethylene may comprise porous polyethylene, high density polyethylene (HDPE) or ultrahigh molecular weight polyethylene (UHMWPE). In some embodiments, polyketones may comprise polyether ketone (PEK), polyether ether ketone (PEEK), or combinations thereof. In some embodiments, polysulfones may comprise polyether sulfone (PES), polyphenol sulfone, or combinations or copolymers thereof. In some embodiments, polymers may comprise silicone.

It is generally desirable that the material be inert to tissue and resistant to degradation over time when in contact with surrounding tissue and fluids. The outer surface 18 of the core may have a texture that is non-porous but generally open enough (or rough enough) to allow the porous cortical layer 20 to mechanically bond to the surface. (This is generally upon application of compression and heat, but other attachment options are possible and considered within the scope of this disclosure.) The center of the core may a more flexible or rigid core.

For manufacturing a hollow implant, rotational molding is one method that may be used to provide a core with a hollow area. In this method, a small amount of material may be added to a mold cavity in the mold is continually rotated and heated. This may result in a porous hollow article.

In another example, the hollow body 16 may be manufactured by cutting a partially processed device in half, and removing the inner contents that are unprocessed and loose in order to form a hollow vessel. The cut halves may be re-assembled and returned to the mold in order to complete the bonding process of the material and rejoin the two halves.

In another embodiment, a blow molded polymer sphere may be provided with a connecting tube during molding that can allow inflation inside a mold cavity in order to produce a hollow sphere that is later sealed with internal pressure.

Figure 6:
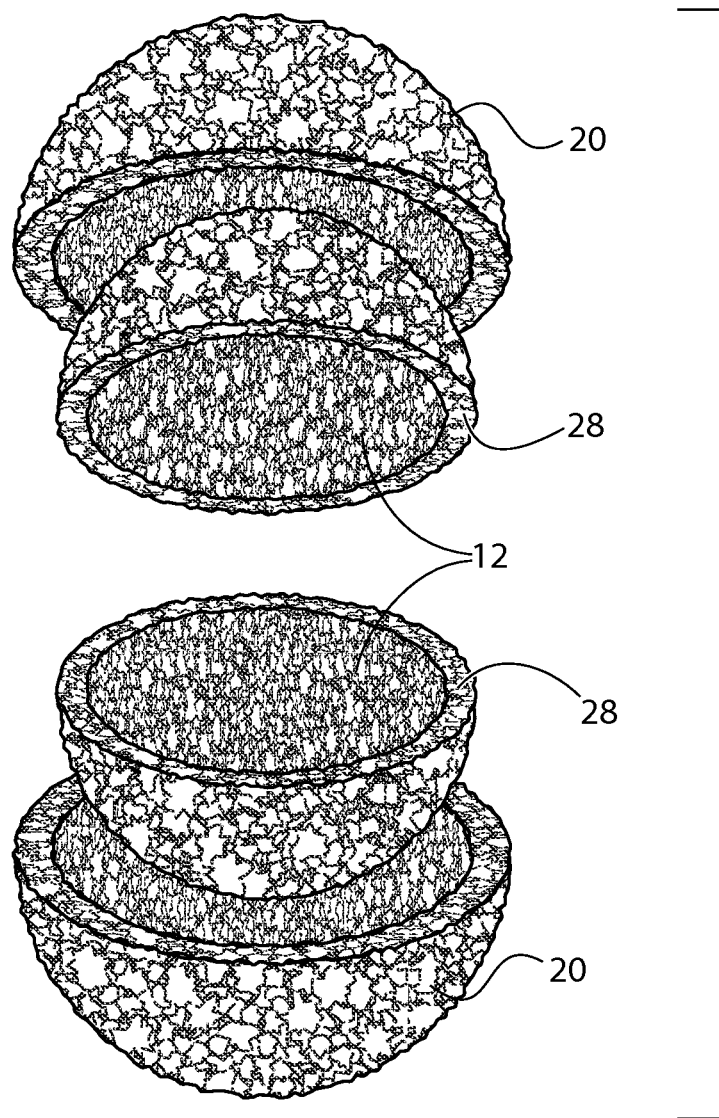
FIG. 6 shows an exploded view of an implant made from two hollow half spheres of a porous material, with a cortical material applied thereto.

In another example, the hollow body 16 may be manufactured by manufacturing two hollow half spheres 28. Examples are illustrated by FIGS. 4-6. In use, the hollow half spheres 28 may be secured to one another in order to provide a hollow body 16 that forms the core 12. It is generally desired for the half spheres 28 to be sealed to one another in use to form the final implant 10. This can help prevent fluid from accumulating within the core 12 and causing rejection or infection. In one example, they may be secured by thermal processing. In the embodiments shown in FIGS. 4-5, the hollow half spheres 28 may be made of generally solid material. In the embodiment shown in FIG. 6, the hollow half spheres 28 may be made of generally porous material.

Figure 10:
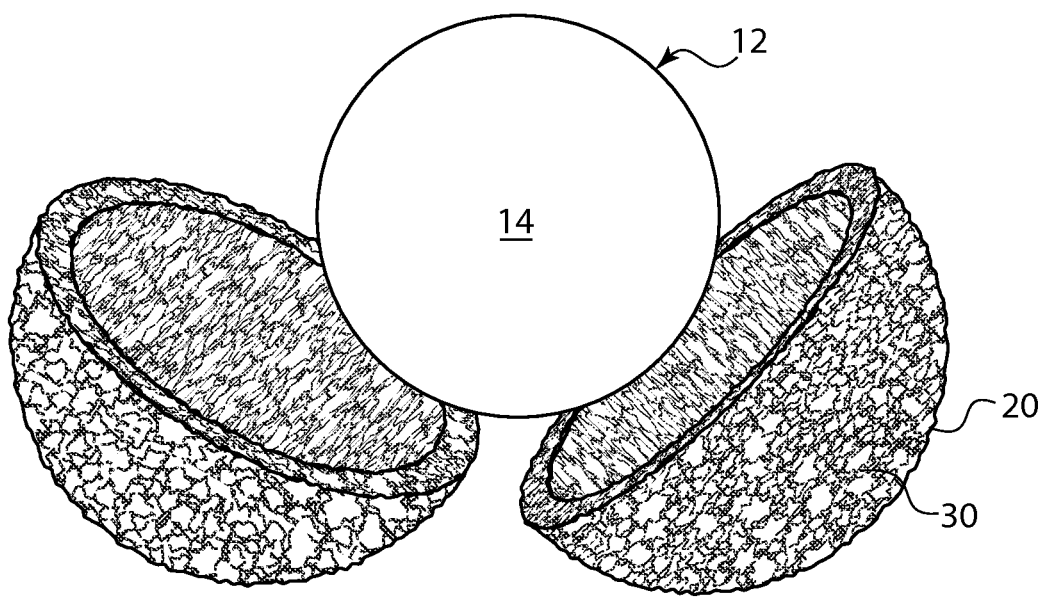
FIG. 10 shows two hollow cortical layer halves to be applied to a solid material core.

In another example illustrated by FIG. 10, the core 12 may be formed as a solid, non-hollow sphere 14 (or as two solid half spheres, if desired). A solid core 14 may be a solid material, such as silicone sphere, a polymer sphere, or any other appropriate material. In other examples, the non-hollow sphere 14 may be made of a porous material, In either case, the non-hollow core may be manufactured by insert molding, injection molding, compression molding (being sintered in a mold), vacuumed molding, blow molding, or any other appropriate manufacturing technique or process.

Figure 11:
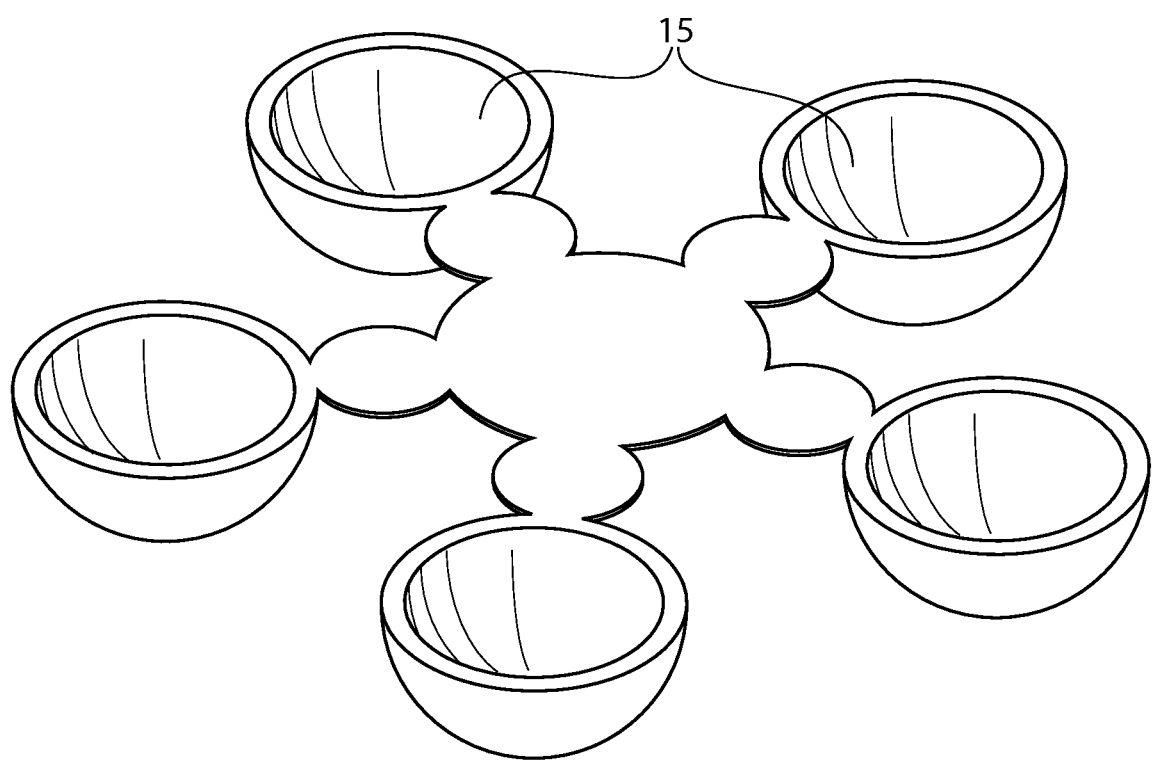
FIG. 11 shows one manufacturing process for providing a plurality of half spheres to form a core.

If the core 12 is provided as solid half spheres 15, the solid half spheres may be formed by blow molding, by insert molding, or by any other appropriate manufacturing technique. One example illustrating a manufacturing method for a plurality of half spheres 15 is shown by FIG. 11. In one embodiment, blow molding may create a sealable spherical shape. The internal pressure of the blow molding process may help overcome shrinkage forces to maintain a desired shape of the final article. The solid half spheres may be formed into a single solid spherical core 12. The halves may be welded together by heat, ultra sonic welding, gamma waves, or any other appropriate technique. Providing half spheres may add to the manufacturability of the device. For some shapes, it may be easier to or necessary to produce two or more halves and reassemble these prior to processing together.

Figure 12:
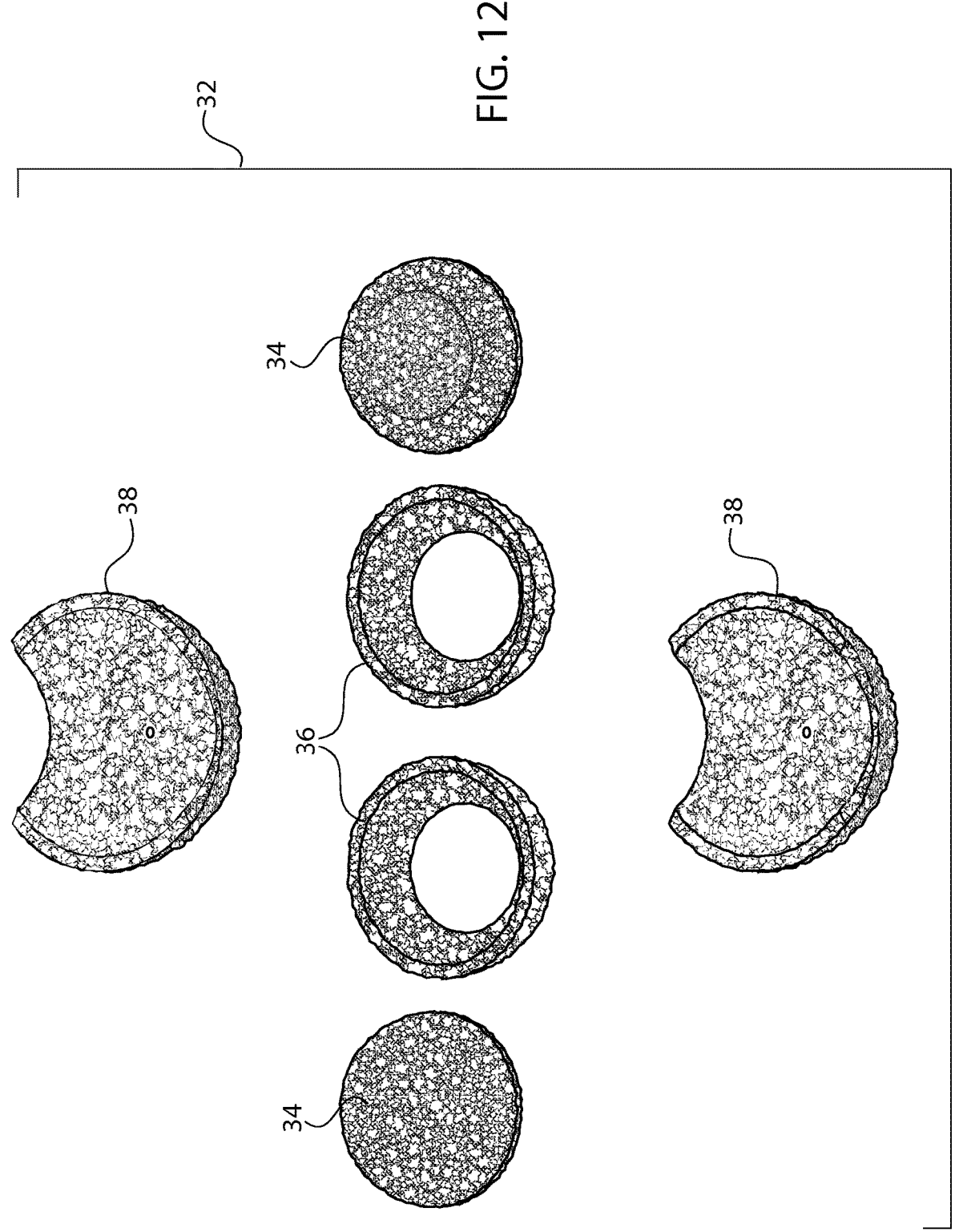
FIG. 12 shows a plurality of individual articles having varying porosities that may be assembled to form an implant.

In another example, the implant 10 may be formed from a plurality of individual articles 32 assembled together. The individual articles 32 may have varying porosities. One example of variously shaped articles 32 is shown in FIG. 12. In this example, there may be provided cap components 34, upper components 36, and equatorial components 38. More or fewer components may be provided. In one example, a center exterior portion/equatorial component 38 of the sphere may have smaller pores than one or more of the other portions. For example, a posterior portion of the implant could be made to be more porous in order to facilitate faster tissue integration. An anterior portion of the implant may have a lower porosity, be smoother, or even be formed to be non-porous. This may help is insertion of the implant 10 into the implant site. Manufacturing an implant 10 using this design can help control locations of desired pore sizes. In fact, some of the individual articles 32 may be solid/non-porous.

Figure 13:
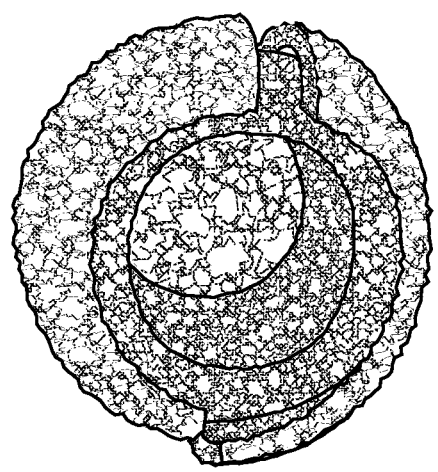
FIG. 13 shows a plurality of individual articles assembled, and prior to application of heat and compression.
Figure 14:
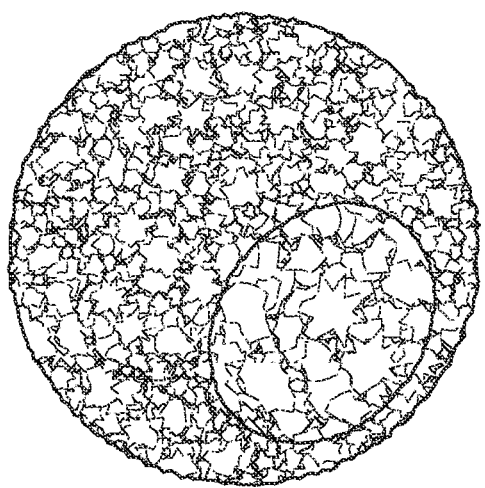
FIG. 14 shows an implant having varying porosities on its porous outer cortical layer.
Figure 15:
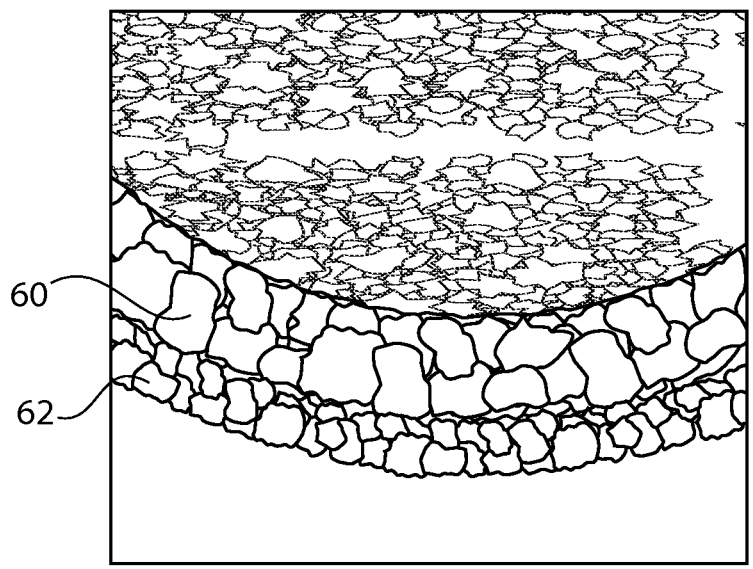
FIG. 15 shows a cross-sectional view of an implant having a porous outer cortical layer varying porosities, with a smaller pore size forming its outermost layer and a larger pore size forming a more inner layer.

FIG. 13 illustrates an assembly of the individual articles 32 prior to being inserted in a mold and thermally processed. Thermal processing results in a one piece composite unit having varying pore sizes. One example of an implant having varying pore sizes on its face is illustrated by FIG. 14. It is possible for the secondary molding operation (referred to as "secondary molding" because the individual articles may be formed by a first molding step) to cause the surface pores to become more compressed together, producing a smoother outer surface 62 with larger internal pores 60 for improved tissue ingrowth. One cross-sectional view of this varying pore size embodiment is illustrated by FIG. 15.

Because it has been found generally desirable for the outer surface 18 of the core 12 to be non-porous to prevent tissue ingrowth, it is possible for the core 12 to be formed in a way that provides a non-porous outer surface 18. For example, the material may be selected so that the pores of the material are so small that they discourage tissue ingrowth. In another example, the material may be selected so that the entire core is non-porous (e.g., the solid or hollow core may be manufactured out of a non-porous material). In another example, it is also possible to secure, bond, adhere, or thermally compress a thin solid membrane to the outer surface of the core, before application of the porous outer cortical layer 20.

The porous outer cortical layer 20 may be formed as two separate components 30 and thermally bonded to the core 12. Examples of this option are illustrated by FIGS. 4-6 and 10. In these examples, the core may be mechanically entrapped within the layer 20. In other embodiments, the porous outer cortical layer 20 may be applied as described above (i.e., as a sintered coating applied around via beads or fines positioned around a core in a mold and exposed to compression and heat). In further embodiments, the porous outer cortical layer 20 may be sprayed, painted, powder coated, or applied to the core 12 using any other appropriate technique. In a further embodiment, the porous outer cortical layer 20 may be applied to core using static charged particles with a grounded mandrel tool to which the particles are attracted to. The implant is then thermally processed in order to produce the desired shape.

The porous outer cortical layer 20 may be provided in any appropriate material. It may comprise polyolefins, polymers, polyamides, polyesters, polyurethanes, polyimides, polyacrylonitriles, polycarbonate, poly methyl methacrylate (PMMA), polytetrafluoroethylene (PTFE), polyvinylidene fluoride (PVDF), polyketones, polysulfones, polyetherimides, or combinations or copolymers thereof. In some embodiments, a polyolefin may comprise polyethylene, polypropylene, or combinations or copolymers thereof. Polyethylene may comprise porous polyethylene, high density polyethylene (HDPE) or ultrahigh molecular weight polyethylene (UHMWPE).

Other examples include polyetherether ketone (PEEK), polyethylene terephthalate (PETE), nylon, polypropylene, or any polymer of aliphatic hydrocarbons containing one or more double bonds, or composites of any of these materials. In some embodiments, polyketones may comprise polyether ketone (PEK), polyether ether ketone (PEEK), or combinations thereof. In some embodiments, polysulfones may comprise polyether sulfone (PES), polyphenol sulfone, or combinations or copolymers thereof. In some embodiments, polymers may comprise silicone. This list is not intended to be limiting, and it should be understood that the porous outer cortical layer may be made from any other appropriate material that can be formed to encapsulate or otherwise cover the core 12 and allow the implant 10 to be at least partially pliable, while also imparting the desired porosity.

In one example, the porous outer cortical layer 20 may have a porous structure with an interconnecting porosity. The pores of this layer may range from about 10 µm to about 1 mm. In a specific embodiment, the average pore size may range from about 100 µm to about 400 µm, from about 150 µm to about 300 µm, from about 200 µm to about 250 µm, from about 300 µm to about 400 µm, or from about 400 µm to about 600 µm. In some embodiments, the average pore size may be at least 20 µm. In another embodiment, the average pore size may be at least 50 µm. In another embodiment, the average pore size may be greater than about 10 µm. In another embodiment, the average pore size may be less than about 1 mm. The pores may be multidirectional interconnected pores.

The materials are generally formed to have an interconnected porous structure (generally referred to as "porous"). The cortical layer 20 may cover greater than 50% of the core, greater than 60%, greater than 70%, greater than 80%, greater than 90%, or greater than 99% of the surface of the core.

In some embodiments, the layer 20 has a porosity ranging from about 20% to about 60%, from about 30% to about 50%, from about 35% to about 40%, or from about 50% to about 60%. In another embodiment, the layer 20 may have a porosity of about 20% or greater. In another embodiment, the layer may have a porosity less than about 60%.

In embodiments in which the core 12 and/or the porous outer cortical layer 20 is polyethylene, it is generally desired that the melt flow index value of the materials be such that the polyethylene sinters upon thermal processing, but does not melt and begin to flow. For example, the melt flow index (MFI) values provided in Table 1 determined at 10 minutes under a 2.16 kg load at 190° C. as detailed in ASTM 1238-65. MFI values of polyethylene may be less than 100 g, less than 50 g, less than 30 g, less than 15 g, less than 10 g, less than 5 g, less than 2 g, or less than 1 g.

In embodiments in which the core 12 and/or the porous outer cortical layer 20 is polypropylene, it is generally desired that the MFI value of the materials be such that the polyethylene sinters upon thermal processing, but does not melt and begin to flow. For example, the MFI values provided in Table 2 were determined at 10 minutes under a 2.16 kg load at 230° C. as detailed in ASTM 1238-65. MFI values of polypropylene may be less than 100 g, less than 50 g, less than 30 g, less than 15 g, less than 10 g, less than 5 g, or less than 2 g.

In embodiments in which the core 12 and/or the porous outer cortical layer 20 is polyetheretherketone (PEEK), it is generally desired that the MFI value of the materials be such that the PEEK sinters upon thermal processing, but does not melt and begin to flow. For example, the MFI values provided in Table 3 were determined at 10 minutes under a 5 kg load at 379° C. as detailed in ISO 1133. MFI values of PEEK may be less than 100 cm³, less than 50 cm³, less than 30 cm³, less than 15 cm³, less than 10 cm³, less than 5 cm³, or less than 2 cm³.

In some examples, it is possible to provide the core 12 and the layer 20 as a being manufactured of the same materials. For example, it is possible to provide an implant 10 having a core 12 with a solid polymer outer surface, and a cortical layer 20 of a porous polymer. In one example, both parts are made of a biocompatible polyethylene.

In another example, the core may be a medical grade silicone with a porous polyethylene cortical layer flexibly molded over the core.

In another example, the core may be silicone and the porous cortical layer may be polyethylene. In one specific example, the core may be silicone with an outer surface having a texture, and the porous cortical layer may be porous polyethylene.

In another example, the core may be polyethylene and the porous cortical layer may be polyethylene. In one specific example, the core may be solid polyethylene and the porous cortical layer may be porous polyethylene.

FIG. 1 illustrates an outer cortical layer 20 of porous polyethylene that is flexibly molded over an inner core material 12. In this example, the inner core material is silicone. In this figure, the silicone core 12 has a molded outer surface texture that allows the porous polyethylene to mechanically bond to the surface of the center core 12.

In another example, the porous outer cortical layer 20 may be formed as two separate components 30. In FIG. 10, the components 30 are shown as hollow half spheres. The components 30 may then be thermally bonded to the core 12. In this example, the core 12 is mechanically entrapped within the two components 30, which form the outer layer 20.

However, it is also possible for the components 30 themselves to form implant 50. One example of this embodiment is illustrated by FIG. 2. In this example, there is not an interior core provided, but instead, the two hollow components 30 may be internally coated or sealed with an internal layer 52 that prevents tissue ingrowth past the coating layer 52. In this implant 50, the two hollow components actually form the porous outer cortical layer 20 on their own.

Additive materials may be included in or on the implant, such as biological or inorganic materials. Exemplary additive materials include but are not limited to bone graft materials, bone or tissue growth promoting substance/osteogenic materials, pharmaceuticals, morphogenetic proteins, silver additives to provide an anti-infection benefit, other transition metals (such as titanium, silver, gold, surgical grade stainless steel, steel coated with titanium, titanium nitride, titanium alloyed with other metals, or mixtures thereof), ceramic/zeolite, calcium phosphates, barium sulfate, imaging contrast agents, materials used to make the implant radiopaque such as beryllium, an inorganic material such as hydroxyapatite or glass, or any combinations thereof. Exemplary osteogenic/bone growth promoting substances include but are not limited to autograft, allograft, xenograft, demineralized bone, synthetic and/or natural bone graft substitutes such as bio ceramics and polymers, osteoinductive factors, or combinations thereof. If the additive material is glass, a representative glass may have a composition comprising by weight 45% $SiO_2$, 24.5% $Na_2O$, 24.5% CaO, and 6% $P_2O_5$. Another exemplary glass may be Bioglass, commercially available from NovaBone products, LLC of Alachua, Fla. If the additive material is a calcium phosphate, it may have a calcium to phosphorus atomic ratio ranging from about 0.5 to about 2.0. Non-limiting examples of calcium phosphates include but are not limited to amorphous calcium phosphate, monocalcium phosphate monohydrate (MCPM), monocalcium phosphate anhydrous (MCPA), dicalcium phosphate dehydrate (DCPD), dicalcium phosphate anhydrous (DCPA), octacalcium phosphate (OCP), alpha-dicalcium phosphate, beta-try calcium phosphate, hydroxyapatite, poorly crystalline hydroxyapatite, tetracalcium phosphate (TTCP), heptacalcium decaphosphate, calcium metaphosphate, calcium pyrophosphate dehydrate, calcium pyrophosphate, carbonated calcium phosphate, or combinations thereof.

Such additives may be included in an amount ranging from up to about 30 wt %. In some examples, additives may be added from about 5 wt % to about 20 wt %, or from about 10 wt % to about 15 wt %. It is possible to include additives in an amount that is greater than about 1 wt %, or in an amount that is less than about 30 wt %.

Such additive materials may be combined with the porous outer cortical layer 20, such that they form a part of the periphery of the implant. Additionally or alternatively, such additive materials may be provided (e.g., packed or injected) within the interior of the implant 10. Materials they be dispersed throughout the matrix of the implant.

The implant may further include openings (foramina), grooves, and/or channels that are intended to permit the transmission of a nerve (such as the optic nerve, ophthalmic nerve, trochlear nerve, a duct such as the nasolacrimal duct, or one or more blood vessels). A channel may also be used to drain a site of excess fluid, such as blood or sample fluid, for analysis. Such openings or channels provided in specific locations may allow the implant to be used over or adjacent to a nerve without causing any impingement or crushing of the nerve when the implant is secured in place.

Figure 16:
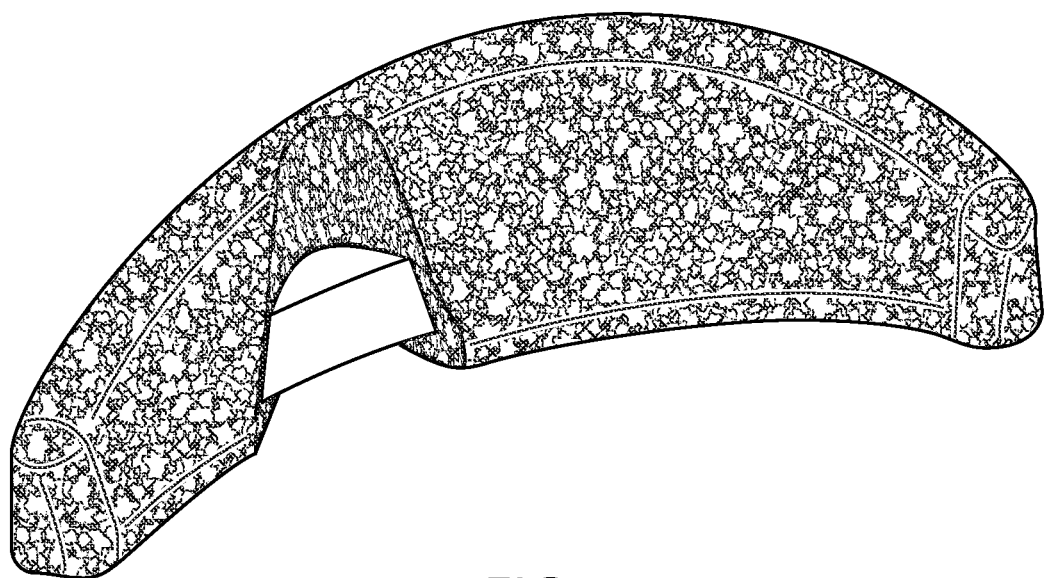
FIG. 16 shows an example of an alternate shape of an implant with a porous outer cortical layer.

Although embodiments of this disclosure have been described with particular reference to ocular implants, it should be understood that the concepts described herein may be used with other surgical implants. For example, it is possible to provide a core material coated with a porous outer cortical layer for other types of implants. Examples include but are not limited to ear reconstruction implants, joint implants, chin and other facial implants, spinal implants, or any other type of implant for which vascular ingrowth is desirable. One example of a potential configuration for one or more of these implants is illustrated by FIG. 16. In this example, the porous outer cortical layer is positioned on a core that is shaped as an ear implant.

In order to manufacture any of the embodiments described herein, the sintering and/or compression temperature may be between about 280° F. to about 360° F. The sintering ad/or compression time may be between 5 minutes up to about 120 minutes. These examples are provided for illustrative purposes only, and are not intended to be limiting in any way.

Changes and modifications, additions and deletions may be made to the structures and methods recited above and shown in the drawings without departing from the scope or spirit of the disclosure or the following claims.

What is claimed is:

1. A non-load bearing ocular implant, comprising:
    a spherical polyethylene core material comprising an outer surface that functions as a barrier to tissue ingrowth;
    a spherical porous polyethylene outer layer sintered to and enclosing the spherical polyethylene core material, wherein sintering results in the core and the outer layer being connected as a one-piece, integral implant, wherein the spherical porous polyethylene outer layer is smooth and allows tissue ingrowth.

2. The implant of claim 1, wherein the spherical polyethylene core material is fully encapsulated by the porous polyethylene outer layer.

3. The implant of claim 1, wherein the spherical polyethylene core material is non-porous and non-hollow.

4. The implant of claim 1, wherein the spherical polyethylene core material is hollow.

5. The implant of claim 1, wherein the spherical polyethylene core material is blow molded, rotational molded, injection molded, or compression molded.

6. The implant of claim 1, wherein the spherical polyethylene core material is provided as two halves that are sealed to one another.

7. The implant of claim 1, wherein the spherical polyethylene core material comprises porous polyethylene, high density polyethylene, ultrahigh molecular weight polyethylene, or combinations thereof.

8. The implant of claim 1, wherein the porous polyethylene outer layer comprises porous polyethylene, high density polyethylene, ultrahigh molecular weight polyethylene or combinations thereof.

9. The implant of claim 1, further comprising one or more additives in the spherical polyethylene core material, in the porous polyethylene outer layer, or both.

10. The implant of claim 1, wherein the spherical polyethylene core material and the porous polyethylene outer layer are thermally processed via heat and compression.

11. The implant of claim 1, wherein in use, fibrovascular ingrowth is allowed to occur into the porous polyethylene outer layer and fibrovascular ingrowth is prevented past the barrier of the spherical polyethylene core material.

12. The implant of claim 1, wherein the spherical polyethylene core material comprises one or more registering features extending from the core prior to application of the porous polyethylene outer layer.

13. The implant of claim 1, wherein the porous polyethylene outer layer has a porosity of about 50 μm to about 700 μm.

14. The implant of claim 1, wherein the porous polyethylene outer layer has a porosity of about 500 μm to about 1500 μm.

15. The implant of claim 1, further containing a radiopaque material to make the implant visible during a CT scan.

16. The implant of claim 1, wherein the implant consists essentially of two components, wherein the core comprises a first component, and wherein the outer layer comprises a second component, wherein the two components are sintered to one another to form the one-piece, integral implant.

17. The implant of claim 1, wherein the outer layer comprises a thickness of about 0.5 mm to about 5 mm.

* * * * *